United States Patent [19]

Ichikawa et al.

[11] Patent Number: 4,668,782

[45] Date of Patent: May 26, 1987

[54] ANHYDROUS CRYSTALLINE OR CRYSTALLINE HEMIHYDRATE MONOHYDRATE OR TRIHYDRATE OF CEPHALOSPORIN DERIVATIVE

[75] Inventors: Yataro Ichikawa, Tokorozawa; Eishin Yoshisato, Iwakuni; Toshiaki Harada, Iwakuni; Hiroshi Imai, Iwakuni; Yoji Suzuki, Hino, all of Japan

[73] Assignee: Teijin Limited, Osaka, Japan

[21] Appl. No.: 817,946

[22] PCT Filed: May 1, 1985

[86] PCT No.: PCT/JP85/00250

§ 371 Date: Dec. 17, 1985

§ 102(e) Date: Dec. 17, 1985

[87] PCT Pub. No.: WO85/05107

PCT Pub. Date: Nov. 21, 1985

[30] Foreign Application Priority Data

May 2, 1984 [JP] Japan .................................. 59-87816

[51] Int. Cl.$^4$ ............................................. C07D 501/46
[52] U.S. Cl. ..................................... 540/222; 540/220
[58] Field of Search .................... 544/20, 22; 540/222

[56] References Cited

U.S. PATENT DOCUMENTS

| | | | |
|---|---|---|---|
| 3,502,663 | 3/1970 | Barnes | 544/20 |
| 3,862,186 | 1/1975 | Silvestri | 544/20 |
| 4,525,473 | 6/1985 | Aburaki et al. | 514/202 |

FOREIGN PATENT DOCUMENTS

| | | | |
|---|---|---|---|
| 0062321 | 10/1982 | European Pat. Off. | 544/22 |
| 1317159 | 5/1973 | United Kingdom | 544/20 |
| 2063871 | 6/1981 | United Kingdom | 544/22 |

*Primary Examiner*—Donald G. Daus
*Assistant Examiner*—Barbara Cassatt
*Attorney, Agent, or Firm*—Sughrue, Mion, Zinn, Macpeak & Seas

[57] ABSTRACT

An anhydrous crystalline, or crystalline hemihydrate, monohydrate or trihydrate of cephalosporin derivative of (6R,7R)-7-[(Z)-2-(2-aminothiazole-4-yl)-2-methoxyiminoacetoamido]-3(1-quinuclidiniummethyl)-3-cephem-4-carboxylate. These crystalline materials can maintain outstanding stability for a very long period of time and afford excellent practical uses as pharmaceutical compounds.

1 Claim, No Drawings

ANHYDROUS CRYSTALLINE OR CRYSTALLINE HEMIHYDRATE MONOHYDRATE OR TRIHYDRATE OF CEPHALOSPORIN DERIVATIVE

TECHNICAL FIELD

The present invention relates to a cephalosporin derivative. More particularly, this invention relates to a crystalline anhydride or a specific hydrate of cephalosporin derivative which has the outstanding stability.

BACKGROUND OF THE ART

The cephalosporin derivatives which have a 2-(2-aminothiazole-4-yl)-2-methoxyiminoacetoamido group at the 7-position are known as the antibiotics having a strong antibacterial activity.

For instance, (6R,7R)-7-[(Z)-2-(2-aminothiazole-4-yl)-2-methoxyiminoacetoamido]-3-(1-quinuclidiniummethyl)-3-cephem-4-carboxylate which is expressed by the following formula

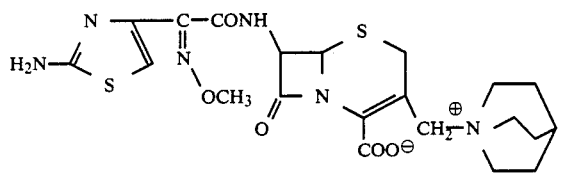

has a betaine structure and this compound is a cephalosporin derivative which has a strong antibacterial activity against Gram-positive and Gram-negative bacterials (Japanese Laid-Open Patent Publication No. 219292/1984), corresponding to U.S. Pat. No. 4,525,473.

Generally speaking, however, these cephalosporin derivatives are chemically unstable since the β-lactam ring in their molecules is liable to be hydrolyzed.

It is, therefore, essentially important to have such cephalosporin derivatives prepared in a stable form when they are to be used as pharmaceuticals.

DISCLOSURE OF THE INVENTION

One of the objects of this invention is to provide a stabilized crystalline (6R,7R)-7-[(Z)-2-(2-aminothiazole-4-yl)-2-methoxyiminoacetoamido]-3-(1-quinuclidiniummethyl)-3-cephem-4-carboxylate or its derivative.

Another object of this invention is to provide a process for the production of a crystalline (6R,7R)-7-[(Z)-2-(2-aminothiazole-4-yl)-2-methoxyiminoacetoamido]-3-(1-quinuclidiniummethyl)-3-cephem-4-carboxylate or its derivative.

A further object of this invention is to provide a novel cephalosporin derivative (6R,7R)-7-[(Z)-2-(5-amino-1-thia-2,4-diazole-3-yl)-methoxyiminoacetoamido]-3-(1-quinuclidiniummethyl)-3-cephem-4-carboxylate.

Other objects of this invention will become apparent from the following description.

These objects and advantages are achieved by a crystalline anhydride, hemihydrate, monohydrate, or trihydrate of a cephalosporin derivative (6R,7R)-7-[(Z)-2-(2-aminothiazole-4-yl)-2-methoxyiminoacetoamide]-3-(1-quinuclidiniummethyl)-3-cephem-carboxylate or (6R,7R)-7-[(Z)-2-(5-amino-1-thia-2,4-diazole-3-yl)-2-methoxyiminoacetoamido]-3-(1-quinuclidiniummethyl)-3-cephem-4-carboxylate.

BEST MODE OF CARRYING OUT THE INVENTION

A cephalosporin derivative which is the subject of the present invention is (6R,7R)-7-[(Z)-2-(2-aminothiazole-4-yl)-2-methoxyiminoacetoamido]-3-(1-quinuclidiniummethyl)-3-cephem-4-carboxylate (hereinafter referred to as a cephalosporin derivative A) expressed by the following formula

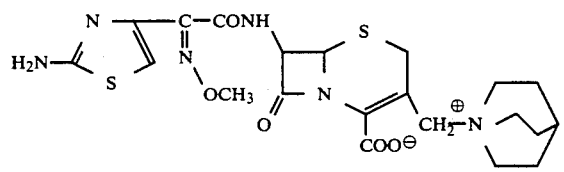

or its derivative, (6R,7R)-7-[(Z)-2-(5-amino-1-thia-2,4-diazole-3-yl)-2-methoxyiminoacetoamido]-3-(1-quinuclidiniummethyl)-3-cephem-4-carboxylate (hereinafter referred to as a cephalosporin derivative B) expressed by the following formula.

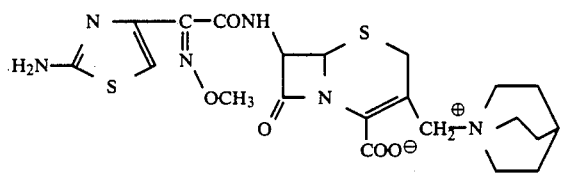

The cephalosporin derivative A or B has a betaine structure in its molecules and a crystalline anhydride, hemihydrate, monohydrate, or trihydrate of such a cephalosporin derivative which has a betaine structure excels others in stability and is suitable for medical use.

A crystalline anhydride, hemihydrate, monohydrate, or trihydrate of cephalosporin A or B can be obtained by dissolving a cephalosporin derivative A or B, which is prepared in an amorphous state, in an aqueous organic solvent, then adding thus obtained solution to an organic solvent or cooling the solution, and further drying the solution, if necessary.

What is referred to as an aqueous organic solvent in the above is a mixture of water and a solvent mixable with water. As the solvent mixable with water, such alcohols as methanol, ethanol, and isopropanol; such ketones as acetone, methyl ethyl ketone, and methyl isobutyl ketone; and such ethers as dioxane and tetrahydrofuran, for instance, are used. They may be used singly or as a mixed solvent. Of the solvents exemplified in the above, alcohols and ketones are preferable. The mixing ratio between said solvents and water may be determined optionally; however, in order to secure the high yield of the desired product, it is advisable to use an aqueous organic solvent containing water at a rate of 95~20 weight %, especially in the range of 90~30 weight %.

A cephalosporin derivative A or B in an amorphous state is made to dissolve in any of the aforementioned aqueous organic solvents. The amount of the cephalosporin derivative A or B to be dissolved can not be defined absolutely since it varies depending upon the quantity of the organic solvent to be added thereto, the temperature of the process, etc.; however, it is usually in the range of 5 to 200 weight %, desirably 10 to 70 weight %.

Next, upon addition of an organic solvent or cooling, a cephalosporin derivative A or B crystallizes out of the solution thus prepared. As the organic solvent to be used here, the abovementioned solvents mixable with water can also be used. Alcohols and ketones are preferable and acetone and methanol are especially recommendable. The amount of such organic solvent to be added to the solution varies depending upon the kind of the solvent to be added; however, it is a general practice to use 2 to 1,000 times in volume of the solution, more preferably 10 to 500 times in volume. The temperature of the process should preferably be kept at room temperature and it is generally recommendable to control the temperature in the range of −10° to 50° C. Upon addition of an organic solvent a crystalline trihydrate of cephalosporin derivative A or B crystallizes out of the solution. It is also possible to have the crystalline trihydrate crystallized simply by cooling the obtained solution without adding an organic solvent. It is desirable to adjust the cooling temperature in the range of −30° to 20° C., especially desirable to keep it at −10° to 10° C.

The precipitated crystals are collected by filtration, washed with any of the aforementioned organic solvents or water, and dried to obtain the desired crystalline trihydrate of cephalosporin derivative A or B.

The trihydrate thus obtained may further be subjected to the drying process to be converted to a monohydrate, a hemihydrate, or an anhydride.

The process of drying may be effectuated in the ordinary drying equipment such as a desicator, drying pistol, and drying oven by use of a common dehydrator such as phosphorus pentoxide, sodium sulfuric anhydride, concentrated sulfuric acid, and calcium chloride.

The drying process can be carried out at atmospheric pressure or under reduced pressure; however, the drying process can be concluded in a shorter time when conducted under reduced pressure. It is a usual practice to carry out the drying at a temperature ranging from 0° to 150° C., preferably in the range of 10° to 90° C.

The trihydrate can thus be converted to a monohydrate, hemihydrate, or even to an anhydride.

A monohydrate, hemihydrate, and anhydride can be converted to a trihydrate by leaving them in the air heavy with moisture.

A crystalline anhydride, hemihydrate, monohydrate, or trihydrate of cephalosporin derivative A or B of this invention can also be produced according to the process described below.

The process of production comprises freezing an aqueous solution of an amorphous cephalosporin derivative A or B prepared, lyophilozation after raising the temperature, and drying, if necessary.

The process starts with the preparation of an aqueous solution of an amorphous product of cephalosporin derivative A or B. The aqueous solution may contain a small amount of such an organic solvent mixable with water as mentioned hereinabove. The solubility of cephalosporin derivative A or B in water is about 30 weight % but it is preferable to adjust the concentration to 20 weight % or more so that the crystallization may be effected efficiently.

It is desirable to add some amount of crystal nucleuses to the aqueous solution beforehand. As the crystal nucleus, a crystalline trihydrate of cephalosporin derivative A or B may be suitable. In this case, it is desirable to have the aqueous solution prepared as a saturated or supersaturated aqueous solution.

Thereafter, the solution is frozen. The freezing temperature should preferably be around −40° C. The time required for freezing usually ranges from 1 to 10 hours.

Then the temperature is raised and thereafter the temperature is usually kept standing at −10° to 0° C. for about 1 to 48 hours. During this time, water and the trihydrate of cephalosporin derivative A or B crystallize to form the respective crystals.

When the crystallization is completed, the crystals are again cooled to about −40° C. and lyophilized according to the ordinary method to give the desired crystalline trihydrate of cephalosporin derivative A or B.

The processing operations described in detail in the above can be practiced in a vial. More particularly, graded amounts of an aqueous solution of amorphous cephalosporin derivative A or B are poured into vials, frozen, and lyophilized after the temperature is raised.

The crystalline trihydrate thus obtained can be converted to a monohydrate, hemihydrate, or anhydride by subjecting it to the aforementioned drying treatment.

The crystaline anhydride, hemihydrate, monohydrate, or trihydrate of cephalosporin derivative A or B is chemically stable and is therefore very suitable for use as pharmaceuticals.

These compounds can be used as injections when filled up in a container such as, for instance, a vial, without or with ordinary adjuvants added thereto as case may require.

The cephalosporin derivative A of the present invention is a publicly known compound and can be produced according to an ordinary method (Japanese Laid-Open Patent Publication No. 219292/1984). The cephalosporin derivative B is a novel compound, which has a strong antibacterial activity against various kinds of Gram-positive and Gram-negative bacterias, and can be produced according to a known method per se (Japanese Laid-Open Patent Publication No. 219292/1984, Japanese patent application No. 58358/1983).

The following examples illustrate the present invention more specifically.

PRODUCTION 1

Production of (6R,7R)-7-[(Z)-2-(2-aminothiazole-4-yl)-2-methoxyiminoacetoamido]-3-(1-quinuclidiniummethyl)-3-cephem-4-carboxylate in an amorphous state 466 mg of (6R,7R)-7-[(Z)-2-(2-trimethylaminothiazole-4-yl)-2-methoxyiminoacetoamido]-3-methyl iodide-3-cephem-4-carboxylic acid benzhydryl ester was suspended in 30 ml of ether and 111 mg of quinuclidine was added thereto. The mixture was stirred thoroughly at room temperature for 1 hour and a half.

The precipitate was filtrated and 3 ml of trifluoroacetic acid was added to the cake (480 mg). After the mixture was stirred at room temperature for 1 hour and a half, trifluoroacetic acid was removed at a temperature below 20° C. under reduced pressure. The residue was crushed in ether, collected by filtration, dissolved in a small amount of methanol, and the solution was separated by use of HP-20 ion exchange resin in the water-methanol mixed solvent system while gradually increasing the volume percentage of methanol from 0% to 40%. The fractions eluted at the volume percentage of methanol ranging from 20% to 40% were pooled and lyophilized to obtain 51 mg of the captioned compound in an amorphous state as desired.

NMR (D$_2$O, ppm) δ:
2.0 ppm (6H, broad);
3.4 ppm (6H, broad triplet);
3.9 ppm (2H, d+d);
4.0 ppm (3H, singlet);
5.35 ppm (1H, d);
5.85 ppm (1H, d);
7.0 ppm (1H, singlet).

PRODUCTION 2

Production of (6R,7R)-7-[(Z)-2-(5-amino-1-thia-2,4-diazole-3-yl)-2-methoxyiminoacetoamido]-3-(1-quinuclidiniummethyl)-3-cephem-4-carboxylate in an amorphous state (i) A suspension of 2.0 g of (6R,7R)-7-amino-3-methyl iodide-3-cephem-4-carboxylic acid in 25 ml of acetonitrile was prepared and 4.4 ml of bistrimethylsilylacetoamido was added to the suspension at room temperature. After the mixture was stirred for 1 hour, it was cooled to −20° C. 0.5 g of quinuclidine was slowly added thereto and the mixture was again stirred at the same temperature for 1 hour to prepare an acetonitrile-trimethylsilyl ester solution of (6R,7R)-7-bistrimethylsilylamino-3-(1-quinuclidinium)methyl-3-cephem-4-carboxylic acid.

Separately, 1.2 g of (Z)-2-methoxyimino-2-(5-amino-1-thia-3,5-diazole-3-yl)acetic acid was made to react with 1.3 g of PCl$_5$ in 10 ml of CH$_2$Cl$_2$ at room temperature in another reaction vessel to prepare liquid acid chloride, which was then added to the above-mentioned solution at room temperature to allow them react with each other. After the mixture was stirred at room temperature for 1 hour, the solvent was distilled away under reduced pressure to obtain 1.35 g of a foam as a residue.

This foam was reslurried thoroughly with 100 ml of water kept at 40° C. and extracted by filtration. The extract was then concentrated and refined on a column of HP-20 ion exchange resin with the use of a mixed solvent of water and acetone, while gradually increasing the volume ratio of acetone from 0 to 40%. 350 mg of an amorphous substance was obtained from the distillate mainly consisting of the captioned compound.

NMR (D$_2$O, ppm) δ:
2.0 (6H, broad);
3.4 (6H, broad triplet);
3.9 (2H, d+d);
4.06 (3H, singlet);
5.25 (1H, d);
5.58 (1H, d).

(ii) The antibacterial activity of the obtained amorphous substance was determined according to the ordinary agar dilution plating method (see the Chemotherapy, 23(8), 1 (1975), of Japan Chemotherapy Society). The result is shown in the following table.

|  | MIC (μg/ml) |
|---|---|
| *Staphylococcus aureus* FDA 209 PJC-1 | 3.1 |
| *Coliform bacillus* NIHJ-JC-2 | 0.05 |
| *Typhoid bacillus* 901 | 0.2 |
| *Bacillus prodigiosus* IAM 1184 | 0.1 |
| *Pseudomonas aeruginosa* IFO 3445 | 0.4 |
| *Proteus vulgaris* OX-19 | 0.2 |
| *Aerobacter aerogenes* ATCC 13048 | 0.1 |

EXAMPLE (1) Preparation of crystalline anhydride, hemihydrate, monohydrate, and trihydrate of (6R,7R)-7-[(Z)-2-(2-aminothiazole-4-yl)-2-methoxyiminoacetoamido]-3-(1-quinuclidiniummethyl)-3-cephem-4-carboxylate (i) An aqueous solution of 10 g of 7-[(Z)-2-methoxyimino-2-(2-aminothiazole-4-yl)acetoamido]-3-[(1-quinuclidinium)methyl]-3-cephem-4-carboxylate in an amorphous state dissolved in 20 g of water was prepared and 20 ml of acetone was further added thereto. The mixture was added dropwise to 3 l of acetone with stirring. The precipitated crystals were separated by filtration, washed with a small amount of water, and subjected to air-drying under the conditions of room temperature and the relative humidity of 40 to 60% to obtain a trihydrate. The result of the moisture determination conducted according to Karl Fischer's method was 9.81% (theoretical value : 9.63%).

The trihydrate thus obtained had the under-mentioned X-ray diffractory characteristics.

| Result of X-ray diffractory | |
|---|---|
| Angle of diffraction (2θ) | Relative intensity (%) |
| 9.6 | 88 |
| 11.1 | 45 |
| 13.6 | 23 |
| 14.5 | 62 |
| 14.8 | 37 |
| 15.1 | 30 |
| 15.4 | 30 |
| 16.0 | 37 |
| 16.4 | 24 |
| 17.6 | 30 |
| 19.2 | 36 |
| 19.7 | 26 |
| 20.5 | 49 |
| 21.6 | 66 |
| 21.9 | 75 |
| 22.4 | 100 |
| 22.9 | 39 |
| 23.3 | 26 |
| 24.2 | 27 |
| 25.1 | 36 |
| 25.5 | 39 |
| 25.9 | 82 |
| 26.8 | 27 |
| 27.2 | 38 |
| 28.1 | 39 |
| 28.9 | 43 |
| 29.8 | 25 |
| 30.5 | 20 |
| 30.8 | 22 |
| 31.1 | 22 |
| 32.1 | 21 |
| 32.8 | 27 |
| 33.2 | 27 |
| 35.6 | 27 |
| 36.2 | 28 |
| 37.1 | 24 |
| 39.1 | 21 |
| 39.4 | 21 |

(ii) The trihydrate was dried under the conditions of 20° C. and 0.1 mmHg in the presence of P$_2$O$_5$ until a constant weight was reached to obtain a monohydrate. The result of the moisture determination according to Karl Fischer's method was 3.50% (theoretical value: 3.43%).

| Result of X-ray diffractory | |
| --- | --- |
| Angle of diffraction (2θ) | Relative intensity (%) |
| 9.7 | 95 |
| 11.1 | 44 |
| 13.6 | 25 |
| 14.5 | 63 |
| 14.8 | 35 |
| 15.1 | 27 |
| 15.5 | 30 |
| 16.0 | 35 |
| 16.4 | 23 |
| 17.1 | 30 |
| 19.2 | 35 |
| 19.8 | 25 |
| 20.5 | 46 |
| 31.6 | 69 |
| 21.9 | 87 |
| 22.4 | 100 |
| 23.0 | 37 |
| 23.4 | 25 |
| 24.3 | 26 |
| 25.2 | 33 |
| 25.6 | 37 |
| 26.0 | 67 |
| 26.9 | 26 |
| 27.3 | 33 |
| 28.2 | 33 |
| 29.1 | 37 |
| 29.9 | 23 |
| 30.6 | 17 |
| 30.9 | 19 |
| 31.3 | 20 |
| 32.2 | 18 |
| 33.2 | 27 |
| 35.8 | 23 |
| 36.3 | 22 |
| 37.6 | 18 |
| 39.1 | 20 |

(iii) The monohydrate was dried at 50° C. in the presence of $P_2O_5$ until a constant weight was reached to obtain a hemihydrate. The result of the moisture determination according to Karl Fischer's method was 1.82% (theoretical value: 1.72%).

| Result of X-ray diffractory | |
| --- | --- |
| Angle of diffraction (2θ) | Relative intensity (%) |
| 9.7 | 100 |
| 11.1 | 51 |
| 13.6 | 29 |
| 14.6 | 64 |
| 14.9 | 42 |
| 15.1 | 31 |
| 15.6 | 37 |
| 16.0 | 41 |
| 16.4 | 29 |
| 19.8 | 36 |
| 19.2 | 42 |
| 19.8 | 31 |
| 20.5 | 53 |
| 21.6 | 60 |
| 22.0 | 92 |
| 22.4 | 96 |
| 23.0 | 42 |
| 23.5 | 26 |
| 24.4 | 32 |
| 25.3 | 30 |
| 25.6 | 36 |
| 26.0 | 58 |
| 27.3 | 33 |
| 29.3 | 37 |
| 30.0 | 22 |
| 30.6 | 20 |
| 31.1 | 20 |
| 31.6 | 21 |
| 32.3 | 21 |
| 33.2 | 24 |
| 35.9 | 20 |
| 36.2 | 20 |

(iv) The hemihydrate was dried at 100° C. in the presence of $P_2O_5$ to obtain an anhydride. The result of the moisture determination according to Karl Fischer's method was 0.21%.

| Result of X-ray diffractory | |
| --- | --- |
| Angle of diffraction (2θ) | Relative intensity (%) |
| 9.7 | 100 |
| 11.1 | 49 |
| 13.6 | 28 |
| 14.6 | 62 |
| 14.9 | 39 |
| 15.1 | 30 |
| 15.6 | 36 |
| 16.0 | 39 |
| 16.4 | 27 |
| 19.8 | 35 |
| 19.2 | 41 |
| 19.8 | 30 |
| 20.5 | 51 |
| 21.6 | 59 |
| 22.0 | 90 |
| 22.4 | 94 |
| 23.0 | 40 |
| 23.5 | 25 |
| 24.4 | 30 |
| 25.3 | 29 |
| 25.6 | 35 |
| 26.0 | 57 |
| 27.3 | 30 |
| 29.3 | 34 |

(v) Upon being allowed to take up moisture, the monohydrate, hemihydrate, and anhydride reversionally converted back to the original trihydrate respectively.

(2) The trihydrate, monohydrate, hemihydrate, and anhydride were sealed up in the brown vials respectively and stored at 85° C. and were analyzed by high performance liquid chromatography later. The result is shown in the following table (residuum percentage: %).

| | Elapse of time | |
| --- | --- | --- |
| Specimen | 10 days later | 24 days later |
| Amorphous substance | 0 | 0 |
| Trihydrate | 97.0 | 86.8 |
| Monohydrate | 96.1 | 85.5 |
| Hemihydrate | 98.3 | 86.3 |
| Anhydride | 97.5 | 86.0 |

INDUSTRIAL APPLICATIONS

The crystalline anhydride, hemihydrate, monohydrate, and trihydrate of cephalosporin derivative of this invention have an outstanding stability and are useful as an anti-bacterial agent.

What we claim is:

1. An anhydrous crystalline, or crystalline hemihydrate, monohydrate, or trihydrate of cephalosporin derivative which is (6R,7R)-7-[(Z)-2-(2aminothiazole-4-yl)-2-methozyiminoacetoamido]-3-(1-quinuclidinium-methyl)-3-cephem-4-carboxylate.

* * * * *